(12) United States Patent
Robertson, Jr. et al.

(10) Patent No.: US 7,623,225 B2
(45) Date of Patent: Nov. 24, 2009

(54) PHOTOMETER WITH MODULAR LIGHT EMITTER

(75) Inventors: Charles W. Robertson, Jr., Centreville, DE (US); Joel B. Hansen, Newark, DE (US); Dale Heintzelman, Wilmington, DE (US); Thomas A. Tokash, Cheapeake City, MD (US); Paul S. Zdinak, Kennett Square, PA (US); Damian W. Ashmead, Middletown, DE (US); Jonathan Pundt, Landenberg, PA (US)

(73) Assignee: Nanodrop Technologies, LLC, Wilmington, DE (US)

( * ) Notice: Subject to any disclaimer, the term of this patent is extended or adjusted under 35 U.S.C. 154(b) by 0 days.

(21) Appl. No.: 12/256,786

(22) Filed: Oct. 23, 2008

(65) Prior Publication Data

US 2009/0103077 A1  Apr. 23, 2009

Related U.S. Application Data

(60) Provisional application No. 60/982,018, filed on Oct. 23, 2007.

(51) Int. Cl.
*G01J 1/04* (2006.01)
(52) U.S. Cl. .................................... 356/218; 356/213
(58) Field of Classification Search ......... 356/213–236, 356/71–73, 440; 250/339.09, 339.12, 252.1, 250/548.1; 362/227, 470; 435/285.2, 461; 422/82.08
See application file for complete search history.

(56) References Cited

U.S. PATENT DOCUMENTS 3,937,614 A * 2/1976 Sodickson et al. ....... 422/82.08
5,751,243 A * 5/1998 Turpin ........................ 342/179
6,628,382 B2   9/2003 Robertson
6,809,826 B2 * 10/2004 Robertson ................... 356/440
6,897,069 B1 * 5/2005 Jarvis et al. ................. 435/461
7,393,681 B2 * 7/2008 Jarvis et al. .............. 435/285.2
7,397,036 B2   7/2008 Robertson et al.
7,434,970 B2 * 10/2008 Machi et al. ................ 362/470
7,486,388 B2 * 2/2009 Buchmann et al. ............ 356/73
2005/0185398 A1 * 8/2005 Scannell, Jr. ................ 362/227

FOREIGN PATENT DOCUMENTS

FR        2 852 694 A1    9/2004
WO    WO 2007/111838 A2   10/2007

* cited by examiner

*Primary Examiner*—Sang Nguyen
(74) *Attorney, Agent, or Firm*—DeWitt Ross & stevens; Charles B. Katz; Michael C. Staggs (57) ABSTRACT

A photometer is provided with modular lighting units wherein each lighting unit includes one or more light emitters. A user may select a desired lighting unit and install it within a photometer base unit, and thereafter activate one or more of the emitters (which may emit light of different wavelengths) to illuminate a specimen. The light provided by the specimen in response can then be captured at a detector, and analyzed to provide an indication of the specimen's characteristics. Different lighting units may optionally include one or more input light adapters (filters or polarizers which modify the light provided by the emitter(s) to the specimen), and/or one or more output light adapters (filters or polarizers which modify the light provided by the specimen to the detector). Users may therefore select lighting units with emitters and light adapters which are particularly suited for detection/analysis of particular specimens and/or components therein.

25 Claims, 5 Drawing Sheets

PHOTOMETER WITH MODULAR LIGHT EMITTER

CROSS-REFERENCE TO RELATED APPLICATIONS

This application claims priority under 35 USC §119(e) to U.S. Provisional Patent Application 60/982,018 filed 23 Oct. 2007, the entirety of which is incorporated by reference herein.

FIELD OF THE INVENTION

The invention relates to the field of photometry (i.e., the measurement of the properties of light, including spectrophotometry, fluorometry, spectrofluorometry, and the like) and the photometric analysis of specimens.

BACKGROUND OF THE INVENTION

A spectrophotometer, a device which measures the intensity of light at its component wavelength(s), is often used to determine characteristics of specimens (usually liquid specimens) in laboratory and other settings. Light, usually in the ultraviolet (UV) and/or visible (Vis) wavelength ranges, is directed through a specimen, and the intensity of the output light at its component wavelengths is compared to the intensity of the input light at its component wavelengths to determine optical characteristics of the specimen (such as absorbance, transmittance, and/or reflectance). One type of spectrophotometer, a fluorescence spectrometer (also known as a spectrofluorometer or fluorospectrometer), also compares input and output light from a specimen, but does so to detect fluorescence, i.e., the emission of light from the specimen at one or more wavelengths owing to the specimen's absorption of light at other (typically shorter) wavelengths. The various measured characteristics—fluorescence, absorbance, transmittance, reflectance, etc.—can then provide information about the identities of the components within the specimen, their relative concentrations, and other features of the specimen.

Spectrophotometers for analysis of small specimens—e.g., specimens having a volume of 2 microliters or less—are becoming increasingly popular owing to their value in the fields of biotechnology and pharmacology, where specimens often tend to be available in very limited quantities. Such spectrophotometers pose design challenges because the small specimen size offers little room for light emission and collection components, and tends to limit the versatility of the spectrophotometers. Some solutions to these challenges are presented in U.S. Pat. Nos. 6,628,382; 6,809,826; and 7,397,036, as well as International (PCT) Patent Application WO2007111838, but it would nonetheless be useful to have spectrophotometers and/or spectrophotometer components (and more generally photometers and/or photometer components) which offer further improvements in versatility.

SUMMARY OF THE INVENTION

Figure 1:
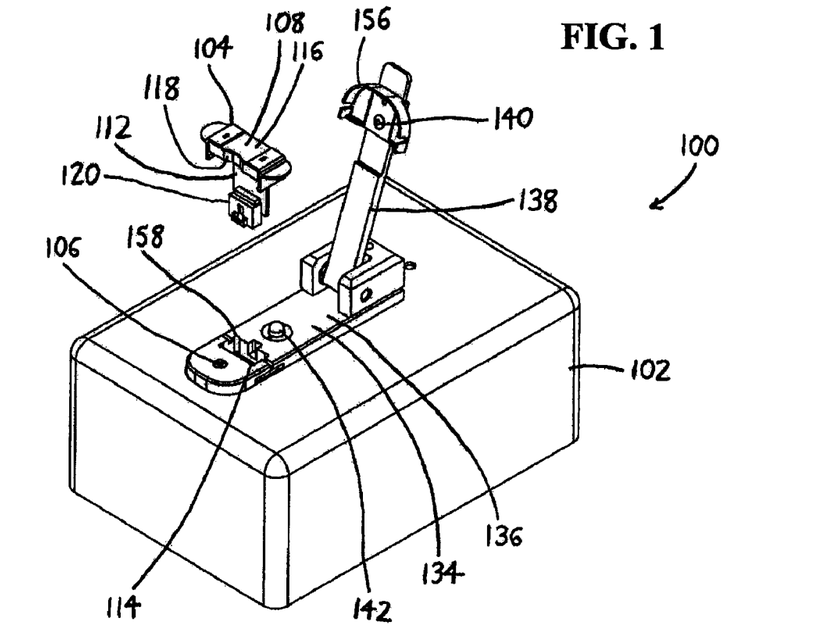
FIG. 1 is a perspective view of an exemplary version of the invention, wherein a modular lighting unit 104 is shown in a position wherein it is ready to be inserted into a socket 114 at the top of a photometer 100 (e.g., a NanoDrop ND-3300 Fluorospectrometer) for analysis of a liquid specimen.
Figure 2:
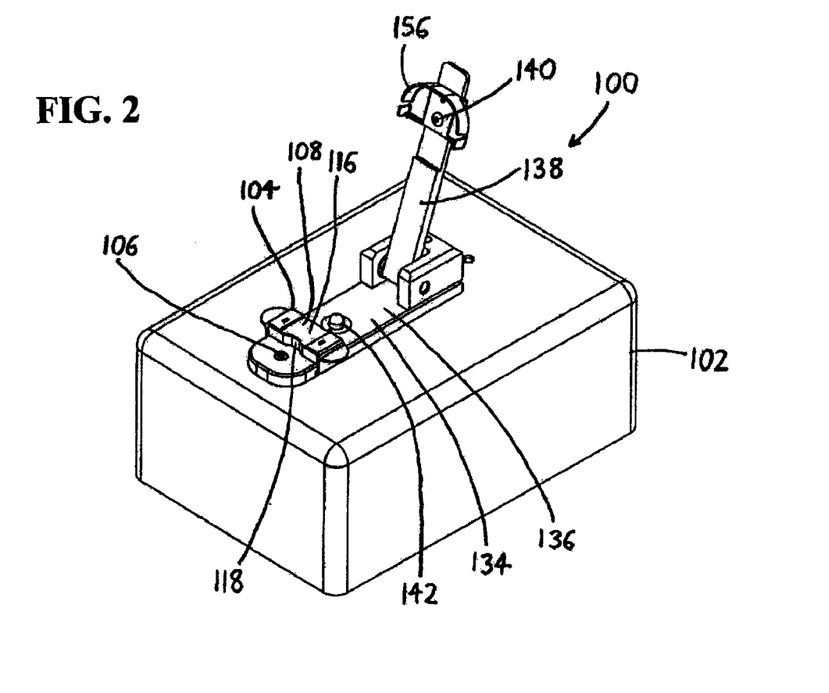
FIG. 2 is a perspective view of the photometer 100 of FIG. 1 wherein the modular lighting unit 104 is installed within the socket 114.

Referring initially to FIGS. 1 and 2, an exemplary preferred version of the invention is depicted generally by the photometer 100. The photometer 100 includes a base unit 102, e.g., a main chassis (preferably sized for desktop use), and one or more removable and replaceable modular lighting units 104 (only one being shown in FIGS. 1 and 2) which are preferably each configured to emit one or more selected wavelengths (or wavelength bands) of light into a fluid specimen situated on a pedestal 106. Different modular lighting units 104 can be configured to emit different wavelengths toward the pedestal 106 and to any specimen thereon. Thus, a user might select a modular lighting unit 104 which is best suited to analyze a component of interest within the specimen (or a component of interest believed to be within the specimen), and install it within the base unit 102 to configure the photometer 100 for analysis of the specimen.

Figure 3:
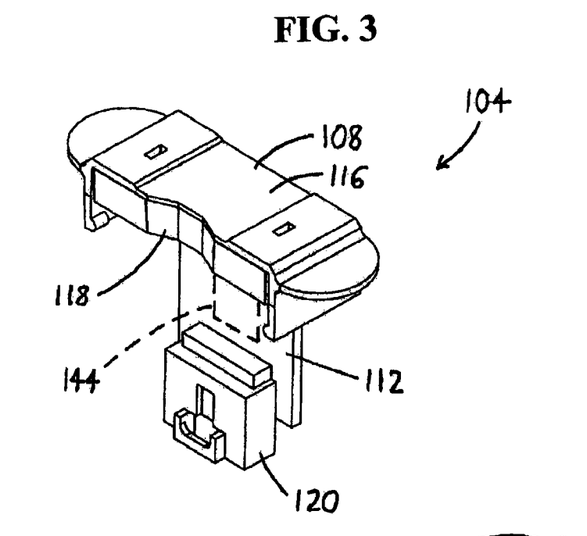
FIG. 3 is a detailed view of the modular lighting unit 104 of FIGS. 1-2.
Figure 4:
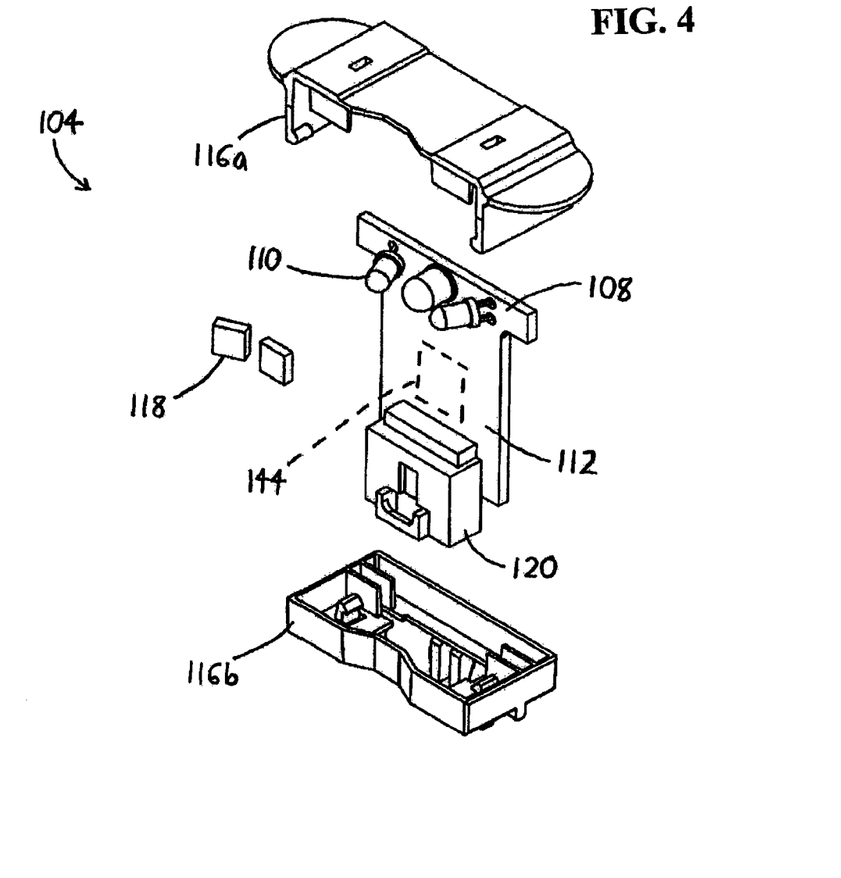
FIG. 4 is an exploded perspective view of the modular lighting unit 104 of FIGS. 1-3.

Referring now to FIGS. 3 and 4, which illustrate the modular lighting unit 104 of FIGS. 1-2 in greater detail, the modular lighting unit 104 includes an emitter end 108 bearing one or more light emitters 110 (FIG. 4, shown in the form of LEDs, though other light-emitting devices could be used), and a communications end 112 extending from the emitter end 108, with the communications end 112 insertable within a socket 114 (FIGS. 1 and 5) extending inwardly from an outer surface of the base unit 102. The emitter end 108 also preferably includes an emitter end frame 116 (shown in sections 116a and 116b in FIG. 4) which at least partially surrounds the light emitters 110, and upon which one or more optical adapters 118 (e.g., filters and/or polarizers) may be mounted adjacent the light emitters 110 to adapt the qualities of the light provided by one or more of the light emitters 110. (In FIGS. 3-4, the emitter end frame 116 is transparent, and thus the light from certain of the emitters 110 is transmitted through the emitter end frame 116 and then through the optical adapters 118 toward the pedestal 106, as best envisioned with respect to FIG. 2.) As perhaps best seen in FIGS. 1-2, the emitter end 108 (and more particularly the emitter end frame 116) is configured such that it cannot fit within the socket 114, whereby the emitter end 108 preferably rests atop the outer surface of the base unit 102 and assists in halting further insertion of the communications end 112 into the socket 114 once the communications end 112 is so fully inserted in the socket 114 that the emitter end encounters the outer surface of the base unit 102.

The modular lighting unit 104 also includes an emitter communications connection 120 (see FIGS. 3-4) in communication with the light emitters 110, wherein the emitter communications connection 120 connects to and receives power and/or signals (e.g., activation signals) from the base unit 102 when the communications end 112 of the modular lighting unit 104 is received within the socket 114 of the base unit 102, thereby allowing activation of light emission from the light emitters 110. FIGS. 3-4 show a preferred arrangement wherein the emitter communications connection 120 is provided on the communications end 112 such that it engages a mating socket connection 122 within the base unit 102 (see FIG. 5) when the communications end 112 of the modular lighting unit 104 is received within the socket 114 of the base unit 102. The emitter communications connection 120 may operate by communicating with two or more leads 124 of the socket connection 122, wherein one or more of the light emitters 110 may be selectively illuminated when power is supplied to a respective set of one or more of the leads 124. Thus, one or more of the emitters 110 may be illuminated to emit light having desired qualities for analysis of a specimen.

Figure 5:
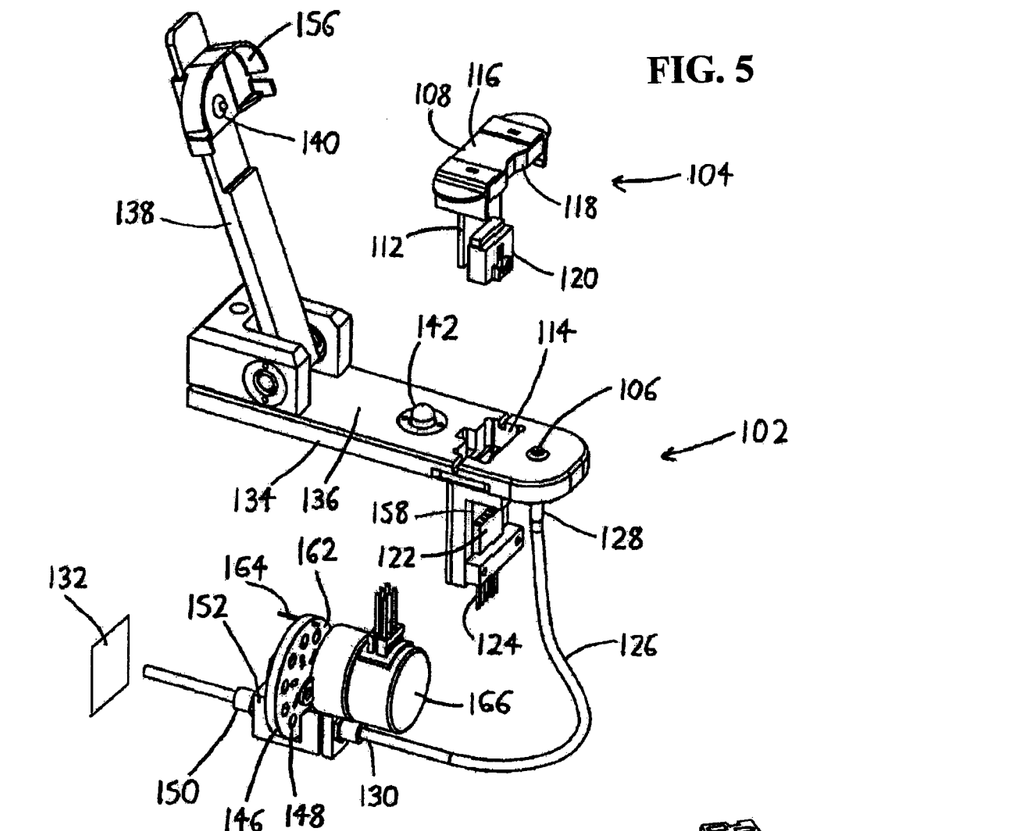
FIG. 5 is a perspective view of the specimen mount 134 (i.e., the base plate 136 and arm 138) of FIG. 1, shown with the modular lighting unit 104 in a ready-to-insert position, and also showing an output optical adapter (a filter wheel 146) for receiving and filtering the output light from the specimen.

As seen in FIG. 1 (and also in FIG. 5, which illustrates the modular lighting unit 104 in conjunction with selected components of the base unit 102), the socket 114 of the base unit 102 is preferably configured to complementarily receive the communications end 112 of the modular lighting unit 104, i.e., the socket 114 is configured to inhibit motion of the modular lighting unit 104 with respect to the base unit 102 other than insertion and removal motion. As a result, once the modular lighting unit 104 is installed in the base unit 102, the emitters 110 will automatically be properly aligned to illuminate the pedestal 106. Referring particularly to FIG. 5, a light transmitter 126 (e.g., a fiberoptic cable or bundle) is also provided in the base unit 102, and it has an input end 128 situated adjacent the socket 114 below the pedestal 106, and an output end 130 supplying light to a detector 132 (e.g., a photosensitive element or other device for measuring qualities of light, such as a spectrometer). Thus, light from a specimen on the pedestal 106 (i.e., light fluoresced from the specimen after light absorption within the specimen, or light otherwise transmitted through or reflected from the specimen) is then at least partially received by the pedestal 106, which is at least partially transparent so that the light is then in turn at least partially received by the detector 132. This light can then be compared to the light transmitted by the illuminated emitter(s) 110 (perhaps after modification by any optical adapters 118), or can otherwise be analyzed, to assist in determining characteristics of the specimen.

As best envisioned with reference to FIGS. 1-2 and 5, the base unit 102 preferably includes a specimen mount 134 which receives the specimen for analysis, with the specimen mount 134 including a base plate 136 situated on the base unit 102 and an arm 138 pivotally linked to the base plate 136. The arm 138 bears a cap 140 which is positioned opposite the pedestal 106 when the arm 138 is swung atop the emitter end 108 of the modular lighting unit 104. When a fluid specimen is pipetted or otherwise supplied to the top of the pedestal 106 (which is preferably oriented at least substantially horizontally so that a small quantity of specimen situated on the pedestal 106 will remain thereon owing to viscous adhesion and force of gravity), the arm 138 can be swung so that the cap 140 contacts the fluid specimen, with the fluid specimen being "sandwiched" between the cap 140 and pedestal 106. The cap 140 can then be respaced with respect to the pedestal 106, as by slightly pivoting the arm 138 upwardly, to adjust the dimensions of the fluid specimen situated on the pedestal 106 (which will tend to form a fluid column between the cap 140 and pedestal 106 owing to surface energy/tension). This in turn can allow better illumination of the fluid specimen by the emitters 110, which are oriented to illuminate the space between the pedestal 106 and cap 140 when the communications end 112 of the modular lighting unit 104 is received within the socket 114 of the base unit 102, and thus better signal strength at the detector 132. The photometer 100 may allow the cap 140 to be automatically or semi-automatically respaced with respect to the pedestal 106, as by providing an actuator 142 situated below the arm 138 and spaced from its pivoting linkage to the base unit 102, wherein the actuator 142 bears against a surface of the arm 138 to vary its pivot angle with respect to the base unit 102 and thus vary the spacing between the cap 140 and pedestal 106.

Figure 9:
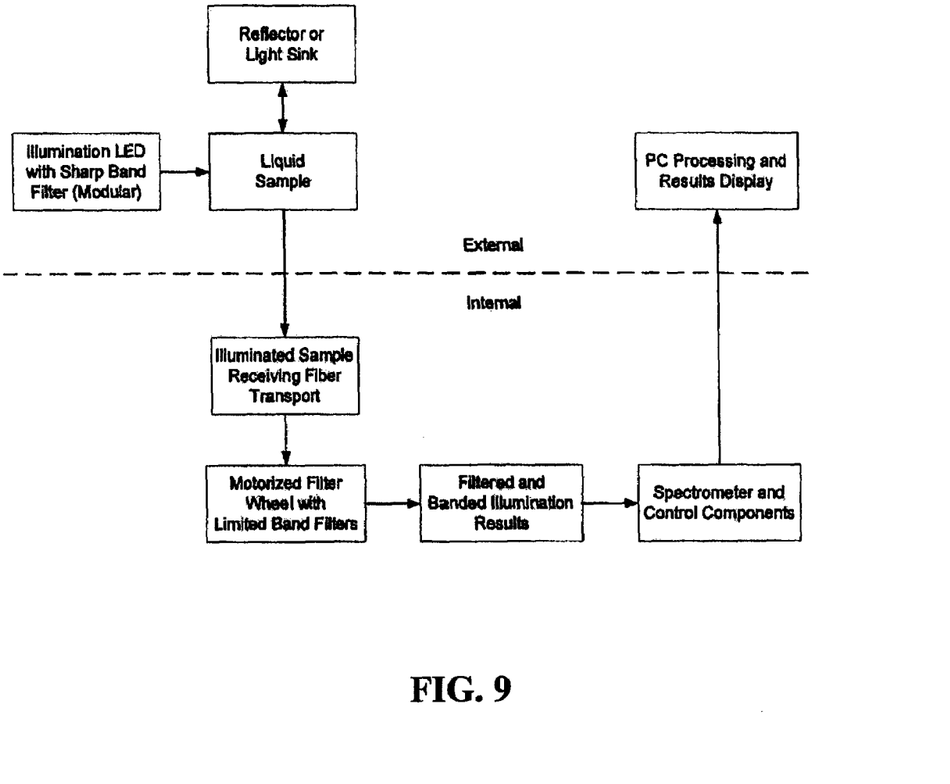
FIG. 9 is a diagram schematically illustrating the components of the exemplary arrangement of FIGS. 1-7 and the information/signals exchanged therebetween.

The pedestal 106 can be provided on the base unit 102 adjacent the light transmitter 126 and socket 114, as shown in FIG. 5 (and FIGS. 1-2), or alternatively it can be provided on the modular lighting unit itself so that it is situated on the base unit adjacent the light transmitter when installed on the base unit. This latter arrangement is exemplified by the arrangement of FIG. 9, wherein a portion of a modular lighting unit 204 is illustrated with two emitters 210, each having an associated optical adapter 218, oriented such that they emit light towards a space situated above a pedestal 206 mounted to the modular lighting unit 204. The light transmitter 226, which is associated with the base unit as with the light transmitter 126 of FIG. 5, then receives light transmitted through the pedestal 206 from the specimen.

As noted above, optical adapters 118 can be situated between the light emitter 110 and the pedestal 106 to better adapt the qualities of the light provided by the emitters 110 to the (known or presumed) characteristics of the specimen atop the pedestal 106, e.g., a narrow band-pass optical filter might provide only a selected range of light wavelengths to a specimen. In similar respects, light provided by the specimen can be modified by optical adapters before it is provided to the detector 132. As a first (and particularly preferred) example, shown in FIGS. 3-4, one or more optical adapters 144 (shown in phantom) might be provided along the communications end 112 of the modular lighting unit 104 (e.g., below the emitter end frame 116 of FIG. 3, but above the emitter communications connection 120), and the light transmitter 126 of FIG. 5 might extend from adjacent the pedestal 106 to terminate at an end directed toward this optical adapter(s) 118 (when the communications end 112 of the modular lighting unit 104 is received within the socket 114 of the base unit 102), and the light transmitter 126 might then resume at the opposite side of the communications end 112 and optical adapter 118 of the modular lighting unit 104 to continue toward the detector 132. In this manner, a modular lighting unit 104 might include both an input (or excitation) optical adapter 118 (i.e., one that modifies the light emitted from the light emitters 110 and input to the specimen), and also an output or emission optical adapter 144 (i.e., one that modifies the light output by the specimen in response).

As another example, looking to FIG. 5, an output optical adapter can be situated between the pedestal 106 and the light transmitter 126, whereby the optical adapter filters and/or polarizes any light transmitted from the pedestal 106 to the light transmitter 126. Such an arrangement can be envisioned with respect to FIG. 9, wherein the pedestal 206 is provided atop a plate-like filter 244.

As yet another example, exemplified by FIG. 5, an optical adapter can be situated downstream from the input end 128 of the light transmitter 126, but upstream from the detector 132. Here, a respositionable filter wheel 146 bears several filters 148, such that a selected one of the filters 148 can be rotatably aligned to receive light from the light transmitter 126. Other arrangements for providing different filters along the light transmission path are possible, as by providing an indexable array of filters (i.e., filters arrayed in a grid or other pattern), and/or by repositioning the ends of the light transmitter 126 on opposite sides of a filter wheel or array about different ones of the filters in the wheel/array.

It should be understood that the invention encompasses not only combinations of photometer base units 102 and modular lighting units 104/204 intended for use with such base units 102, but also components of this combination, e.g., it encompasses modular lighting units 104/204 standing alone, as well as base units 102 which are designed to receive modular lighting units 104/204, or which otherwise have characteristics discussed in this document. Further, the invention encompasses subassemblies of base units 102 and modular lighting units 104/204.

Further advantages, features, and objects of the invention will be apparent from the remainder of this document in conjunction with the associated drawings.

DETAILED DESCRIPTION OF PREFERRED VERSIONS OF THE INVENTION

To review and amplify the discussion given in the Summary above, referring particularly to FIGS. 1, 2, and 5, the exemplary photometer 100 includes a specimen mount 134—this term being used to refer to a base plate 136 bearing the socket 114, and an arm 138 pivotally linked to the base plate 136—which allows a liquid specimen to be mounted adjacent the modular lighting unit 104 (when installed as in FIG. 2) for illumination. The arm 138, which includes a specimen cap 140, may be swung downwardly over a pedestal 106 situated on the base plate 136 adjacent the socket 114 which receives the modular lighting unit 104. The pedestal 106 is situated such that it is coaxially aligned with the cap 140 when the arm 138 is swung downwardly atop the specimen mount 134 base plate 136. When the specimen is situated on the pedestal 106 (e.g., when a small volume of liquid specimen is pipetted or otherwise placed onto the pedestal 106), it is prepared for illumination by the (installed) lighting unit 104 by swinging the arm 138 downwardly until the cap 140 comes in contact with the liquid specimen on the pedestal 106. An actuator 142 situated below the arm 138 on the base plate 136 may then minutely rise (or drop) to adjust the angle of the arm 138 so that the desired spacing can be attained between the pedestal 106 and the cap 140. This adjusts the shape of the liquid mass of the specimen, which adheres to and extends between the pedestal 106 and the cap 140 owing to its viscosity and surface tension. The actuator 142 thereby allows adjustment of the shape of the liquid "column" suspended between the cap 140 and pedestal 106, and allows adjustment of the path length of the light emitted by the lighting unit 104 through the specimen.

The cap 140 on the arm 138 is partially surrounded by a hood 156 which, when installed over the pedestal 106 adjacent the emitter end frame 116, defines a compartment about the fluid specimen suspended between the pedestal 106 and cap 140 to better isolate the specimen from extraneous light (i.e., from light other than that from the emitter(s) 110). The interior of the hood 156, as well as areas of the emitter end frame 116 and of the outer surface of the base unit 102 which rest adjacent the hood 156, are preferably coated or otherwise given an absorptive/non-reflective surface to better limit the light emitted onto the fluid specimen to light emitted directly from the emitter(s) 110.

Referring to FIG. 2, if one envisions the arm 138 swung downwardly so that a liquid specimen is situated between the pedestal 106 and the cap 140, measurements are taken from the specimen by emitting light from the concave area at the front of the lighting unit 104 toward the specimen. Light enters the specimen along a horizontal axis, and the light output from the specimen then travels downwardly along a vertical axis into the pedestal 106. The pedestal 106 is defined by the end of a light transmitter 126 such as a fiberoptic cable (as best seen in FIG. 5), or by optically transmissive components situated at or adjacent the end of the light transmitter 126, so that the pedestal 106 may receive and further transmit the output light from the specimen. The output light is then supplied by the light transmitter 126 to an output filter, here taking the form of a filter wheel 146 (FIGS. 6-7) having a number of filters so that the output light is filtered as desired by a selected filter 148. The filtered output light is then transferred along the remainder of light transmitter 126 to a detector 132, which provides measurements of the intensity of the filtered output light at some or all of its component wavelengths.

It is then useful to review the structure and function of the lighting unit 104 in greater detail. Referring particularly to FIG. 4, the lighting unit 104 has a lower communications end 112 which fits into the socket 114 of the base unit 102 (as shown in FIG. 1), and a top emitter end 108 (bearing upper and lower emitter end frames 116a and 116b) which rests atop the base plate 136 when the communications end 112 is within the socket 114. The communications end 112 bears at least one, and preferably several, light emitters 110 (e.g., LEDs), which are affixed in electrical communication with connector 120. The upper portion 116a of the emitter end frame 116 fits atop the communications end 112 and its light emitters 110, and the lower portion 116b of the emitter end frame 116, which is preferably formed of translucent materials, is then fit upon the communications end 112 about and below the emitters 110. As a result, light from one or more of the emitters 110 may be passed through the lower portion of the emitter end frame 116b and to a specimen between the pedestal 106 and cap 140 with little or no attenuation or other alteration. However, the outer face of the lower portion of the emitter end frame 116b may bear one or more optical adapters 118 thereon (e.g., filters, polarizers, etc.) if alteration of the output of one or more of the emitters 110 is desired. In particular, it is useful to include optical adapters 118 which serve as "sharp" bandpass filters, i.e., bandpass filters which pass only a narrow range of wavelengths. In this manner, the light output from an emitter 110 can be adapted to effectively rest within a selected wavelength band by use of a suitable adjacently-situated optical adapter 118.

Referring to FIG. 5, it is seen that the socket 114 opens onto a downwardly-extending slot/track 158 which ends in a connector 122 for mating with the connector 120 of the lighting unit 104. This connector 122 is connected in communication with a suitable controller and power source, neither of which are shown. As the lighting unit 104 is inserted into the socket 114, the lower communications end 112 (FIG. 4) and connector 120 are received within the socket 114 and guided by the track 158 so that the connector 120 of the lighting unit 104 affixes in communication with the connector 122 of the socket 114. When the lighting unit 104 is fully received within the socket 114, the lower emitter end frame 116b (FIG. 4) and emitters 110 are situated atop the base plate 136 (see FIG. 2) of the specimen mount 134, and they face the pedestal 106 at a predefined distance from the pedestal 106 (and thus at a predefined distance from any specimen situated between the pedestal 106 and the cap 140 of the arm 138).

Figure 6:
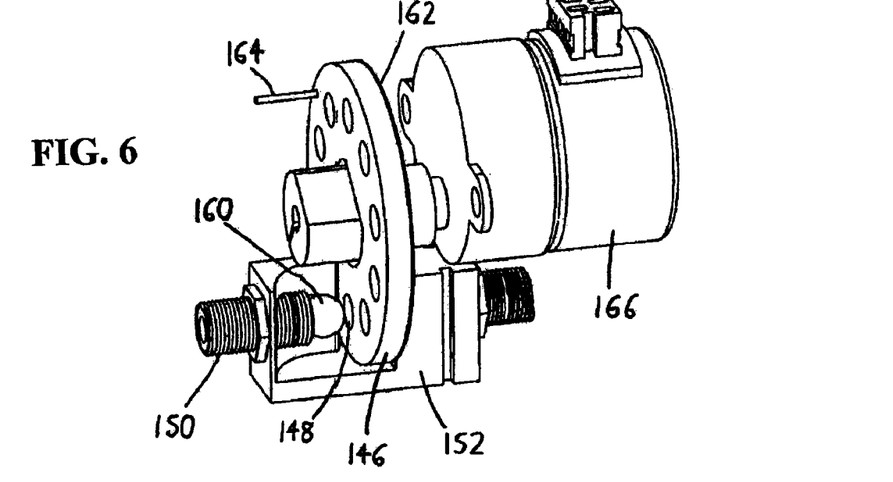
FIG. 6 is a detailed view of the filter wheel 146 of FIG. 5, showing the filter wheel 146 interposed between fittings 150 (which are situated at the opposing ends of the light transmitter 126 shown in FIG. 5) within a wheel receiver 152 (shown partially cut away).
Figure 7:
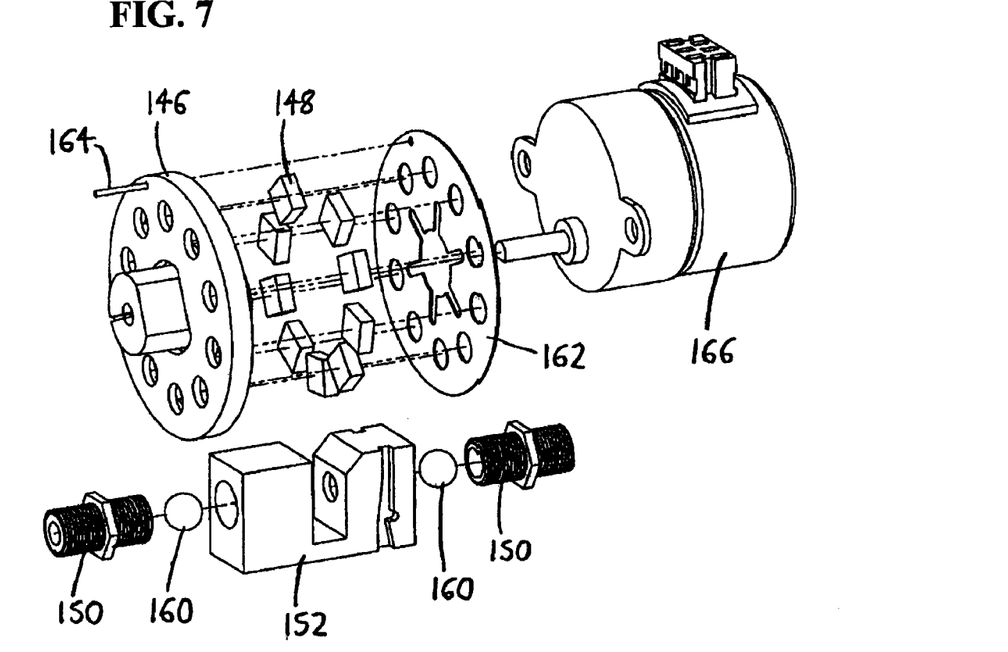
FIG. 7 is an exploded perspective view of the output optical adapter 118 of FIGS. 5-6.

Referring next to FIGS. 6 and 7, the fittings 150 receive the light transmitters 126 (shown in FIG. 5), and direct light between them through lenses 160 (e.g., ball lenses) and through the filter wheel 146. Looking to FIG. 7, the filter wheel 146 bears a series of cavities on its rear (not shown) for receiving a variety of filters 148, each of which may be configured to pass a desired range of wavelengths. The filters 148 are preferably maintained in place within the filter wheel 146 via an attachment plate 162 which sandwiches the filters against the filter wheel 146. The front face of the filter wheel 146 also bears a protruding stop 164 which interferes with (cannot rotate through) the wheel receiver 152, and thereby helps to set a datum or zero position for the filter wheel 146. A motor 166 (e.g., a stepping motor) rotationally drives the filter wheel 146 within the wheel receiver 152 so that a desired filter 148 may be aligned between the ball lenses 160, the fittings 150, and the light transmitters 126 (shown in FIG. 5). Preferably, the motor 166 has a number of discrete poles/steps/positions such that when the motor 166 is activated, it can step or "snap" from one pole/step/position to another, with the filters 148 each being aligned relative to a pole/step/position such that each filter 148 can be snapped into alignment with the ball lenses 160 and fittings 150.

Referring back to FIG. 1, the photometer 100 is preferably powered by, and control signals are communicated through, a USB (Universal Serial Bus) or other connection which communicates with a personal computer or other programmable device. Thus, an appropriate software program or other instruction set running on the programmable device can activate one or more of the desired emitters 110 (FIG. 4) of the lighting unit 104 to illuminate a specimen, select and index to a desired output filter 148 in the filter wheel 146 (FIGS. 6-7) to filter the output light, collect output wavelength and intensity data from the detector 132 (FIG. 5), etc. Preferably, the control system includes an option whereby a user can override automatic selection of an output filter 148 and select whatever output filter 148 the user desires. In the situation where the emitter(s) 110 are coupled with corresponding output filter(s) 144 on the lighting unit 104 (FIGS. 3-4), selection of the lighting unit 104 might automatically select the output filter(s) 144.

It is contemplated that the photometer 100 will be provided to users with a number of different lighting units 104 which each bear one or more emitters 110 having different emission wavelengths and/or different intensities, so that users may select and install lighting units 104 which are better adapted for analysis of the specimen at hand. For example, one lighting unit 104 might bear three emitters 110 which each emit different wavelength ranges, and one or more of these emitters 110 may be activated during specimen analysis to supply input light along the selected wavelength range(s). Another lighting unit 104 might bear two or more emitters 110 which emit the same wavelength range(s) so that the lighting unit 104 is capable of emitting these wavelengths at varying intensity levels depending on how many of the emitters 110 are illuminated.

As noted previously, in the version of the photometer illustrated in FIG. 5, when a selected lighting unit 104 is installed within the socket 114, the control system of the photometer 100 will automatically recognize the lighting unit 104 (i.e., the wavelengths that may be emitted by the emitter(s) 110 of the lighting unit 104), and will index the filter wheel 146 to a suitable filter 148 which is complementary to the wavelength(s) to be emitted. This identification can be performed in one or more ways. Initially, when a reference sample (such as distilled water) is situated in the specimen receiving area between the pedestal 106 and the cap 140, one or more of the emitters 110 can be activated to illuminate the reference sample. A selected one of the filters 148 (FIG. 7) can be situated along the optical path, preferably a filter 148 which passes a wide band of wavelengths (or more preferably a "filter" which is simply optically transparent, and which provides no true filtering at all). The resulting light can then be supplied to the detector 132 via light transmitter 126 (FIG. 5) so that its component wavelengths and intensities may be measured, thereby characterizing and identifying the emitter(s) 110 of the selected lighting unit 104. Alternatively or additionally, the lighting unit 104 might bear a chip or other components (e.g., within the connector 120 of FIG. 4) which give each lighting unit 104 a unique "signature" corresponding to its unique set of emitters 110. As a simple example, the connector 120 might bear one or more resistors which display a unique resistance (as measured across one or more leads 124 of the connector 122 in FIG. 5), with the unique resistance value corresponding to the unique set of emitters 110 (FIG. 4) within the lighting unit 104. With this arrangement, the controller for the photometer 100 may identify the chosen lighting unit 104 and its emitter(s) 110 once the lighting unit 104 is inserted within the socket 114, without the need to activate the emitter(s) 110 for measurement of their output.

The description set out above is merely of exemplary preferred versions of the invention, and it is contemplated that numerous additions and modifications can be made. Following is a review of some exemplary modifications.

The lighting unit 104 discussed above is shown implemented within a spectrophotometer such as the NanoDrop ND-3300 fluorospectrometer (Thermo Fisher Scientific, Wilmington, Del., USA). However, it should be understood that modular lighting units may be implemented in photometers (including fluorometers, spectrophotometers, spectrometers, etc.) having different configurations and different modes of operation, e.g., in the photometers noted in the patents and publications noted previously in this document. Such photometers may bear only a single pedestal for analysis of a single specimen at any given time, or multiple pedestals (and accompanying emitters, etc.) for analysis of multiple specimens at any given time. Additionally, pedestals (and caps) may vary in their configuration and properties, e.g., they may be hydrophilic or hydrophobic, convex or concave, etc., to better accommodate liquid specimens of different types (it being understood that "liquid" specimens can encompass gels/pastes, suspensions/emulsions, or other matter which does not immediately or readily flow at standard environmental conditions). Versions of the invention have also been contemplated wherein the arm 138, once situated adjacent the pedestal 106, is not raised and lowered by the actuator 142 to change the configuration of the fluid column to be formed between the pedestal 106 and the cap 140. Rather, the pedestal 106 is situated on a moving stage to raise or lower it with respect to the cap 140.

Additionally, it should be understood that the particular configurations of the lighting units 104/204 depicted in the drawings are merely exemplary, and lighting units may take forms having appearances which are vastly different from the ones depicted. As an example, a lighting unit might simply take the form of a cartridge having a box-like, cylindrical, or other configuration having an at least substantially uniform circumference, and which inserts within a complementary socket in a base unit to connect to and communicate with the base unit. However, it is preferable to include "wings" atop the lighting unit (as exemplified by the protruding portions of the emitter end frame 116 atop the communications end 112 in FIGS. 3-4), or other readily grasped structure, so that a user may more easily remove and replace lighting units. The socket in the base unit receiving the lighting unit need not necessarily be deeply recessed within the base unit, and the socket could (for example) be defined on the surface of the base unit between structures protruding from the surface of the base unit. Additionally, the power and/or communications connections between the lighting unit and base unit need not be within the socket. Arrangements which are the converse of the foregoing arrangements are also possible, i.e., light emitters may be situated on lighting units bearing sockets, with such lighting units then being installable on plug-like structure on the photometer. Also possible are hybrid arrangements wherein the lighting units bear both male and female structural features which then complementarily mate with female and male structure on the photometer.

Moreover, lighting units need not necessarily be installed within sockets in the base unit, and could instead (or additionally) be installed in other components. As an example, looking to FIGS. 1-2, an emitter could be situated on the arm 138 adjacent the cap 140, preferably on a modular lighting unit which is received on the arm 138 so that the emitter within the modular lighting unit illuminates the fluid column to be formed between the pedestal 106 and the cap 140. Such a modular lighting unit might be received within a complementary socket on the arm 138, or a portion of the arm 138 might be received within a socket in the modular lighting unit, or combinations of such arrangements might be used.

One configuration of a lighting unit of this nature which is expected to be useful is one wherein two or more emitters on the arm 138 have the same emission intensities and wavelength ranges, and wherein they are each provided with a respective polarizer, with each polarizer being of a different type (e.g., one generating light polarized along one plane, and another generating light polarized along a perpendicular plane). The controller for the photometer might then alternately activate the emitters in at some frequency, with one emitter being on when the other is off, and can monitor the detector's output in response to the varying polarization of the input light. To enhance this response, an output polarizer is preferably also situated somewhere along the path of the light output from the specimen, e.g., within the pedestal (such as a specially-adapted pedestal that may be installed in the base plate of the specimen mount), or atop the pedestal (between the specimen and the pedestal) or downstream from it (though in these cases the pedestal and any downstream components prior to the polarizer should be chosen to maintain the polarization of the light received by the pedestal). The output polarizer is preferably oriented with its planes of polarization parallel to one of the emitters, and perpendicular to the other. This arrangement can (for example) indicate changes in anisotropy and/or polarization of molecules within the specimen, and the speed at which changes occur. To illustrate, if a specimen bears a solution of proteins and fluorophores which bind to the proteins, as the fluorophores bind, their Brownian motion/rotational speed (and those of the proteins) within the solution may change, resulting in changes in anisotropy and/or polarization, and changes in response to polarized light. Thus, changes in the monitored output light can give an indication of the speed and degree of fluorophore binding within the specimen.

Figure 8:
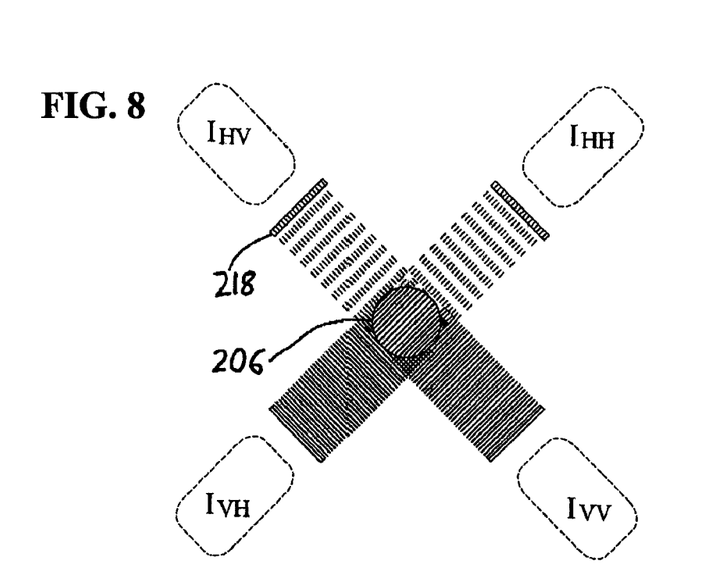
FIG. 8 is a schematic depiction of an arrangement for measuring the anisotropy of a specimen, wherein light emitters $I_{HV}$, $I_{HH}$, $I_{VH}$, and $I_{VV}$ surround a specimen on a pedestal 206 to illuminate it with light polarized in different planes (as generated by input optical adapters/polarizers 218).

An example of such an arrangement is schematically illustrated in FIG. 8, which shows a set of four light emitters labeled $I_{HV}$, $I_{HH}$, $I_{VH}$, and $I_{VV}$, which might be borne on the arm 138 of FIGS. 1-2, and which surround the pedestal (here denoted 206) to illuminate any specimen thereon when the arm is appropriately positioned. (Alternatively, these emitters might be situated on the base unit adjacent the pedestal, possibly in one or more modular lighting units received in the base unit so long as the lighting units and base unit are appropriately configured.) The emitters are preferably identical, i.e., they have the same emission wavelength and intensity, and each has an input polarizer 218 receiving its light output. These input polarizers 218 are oriented such that their planes of polarization are oriented orthogonally to each other as schematically depicted in FIG. 8. The pedestal 206 (or some component downstream from the pedestal 206) is made of optically transmissive polarizing material as well. When the specimen is illuminated by sequential polarized light emissions from the emitters $I_{HV}$, $I_{HH}$, $I_{VH}$, and $I_{VV}$, the differences in the measured output light generated from the differently-polarized input light can provide an indication of anisotropy and polarization as follows (where $I_{HV}$, $I_{HH}$, $I_{VH}$, and $I_{VV}$ here represent the measured intensity of the output light from the specimen from the emitters of the same name):

$$G = \frac{I_{VV}}{I_{HH}}$$

$$\text{Anisotropy } r = \frac{I_{VV} - GI_{VH}}{I_{VV} + 2GI_{VH}}$$

$$\text{Polarization } P = \frac{I_{VV} - GI_{VH}}{I_{VV} + GI_{VH}}$$

(If the emitters $I_{HV}$, $I_{HH}$, $I_{VH}$, and $I_{VV}$ do not in fact have the same emission intensity, the foregoing calculations require correction to account for unequal light input to the specimen.)

Also, as implied by the discussion above, multiple lighting units might be installed simultaneously if they are appropriately sized and configured, with selected ones being chosen for use. Thus, in FIGS. 1-2, multiple lighting units could be installed in multiple sockets surrounding the pedestal 106 (with such multiple lighting units and sockets being configured differently than those shown), and selected ones can be activated when desired. Empty or unused sockets might be plugged by "dummy" lighting units if such an arrangement offers advantages (e.g., to protect the interior of the socket, to better protect the mounted specimen and/or to support the arm 138, etc.).

Further, the optical arrangements depicted in the drawings are merely exemplary, and can assume a variety of other forms. Some or all of the light transmitter 126 may take the form of a fiberoptic cable or any other light-transmitting medium or arrangement, including the possibility of directing the light signal through free space between spaced lenses, mirrors, and/or prisms. As noted previously, the lighting unit 104 may bear an output optical adapter 144 (FIGS. 3-4) as well as (or instead of) an input optical adapter 118, and a portion of the light transmitter 126 (FIG. 5) might extend from adjacent the pedestal 106 to a location adjacent the output optical adapter 144, with another portion of the light transmitter 126 then resuming on the opposite side of the output optical adapter 144 to continue to the detector 132. In this case, the portion of the light transmitter 126 extending between the pedestal 106 and the output optical adapter 144 might be provided on the lighting unit 104 (e.g., as a light-transmitting prism mounted on the communications end 112). The pedestal 106 might also be provided on the lighting unit 104 in this case, and the aforementioned light transmitter might be integrally formed with the pedestal 106 (and/or with the output optical adapter 144).

It should be understood that the versions of the invention described above are merely exemplary, and the invention is not intended to be limited to these versions. Rather, the scope of rights to the invention is limited only by the claims set out below, and the invention encompasses all different versions that fall literally or equivalently within the scope of these claims.

What is claimed is:

1. A photometer including:
   a. a base unit having:
      (1) a detector;
      (2) a light transmitter directing light from a transmitter input end toward the detector; and
      (3) a socket extending inwardly from an outer surface of the base unit, the socket being situated adjacent the transmitter input end;
   b. a modular lighting unit having:
      (1) a communications end configured to be complementarily received within the socket of the base unit;
      (2) an emitter end adjacent the communications end, the emitter end including a light emitter aligned to emit light outwardly from the emitter end toward the light transmitter when the communications end is received within the socket of the base unit; wherein the modular lighting unit is removable from, and replaceable within, the socket of the base unit;
   c. a pedestal whereupon a specimen being situated, the pedestal being:
      (1) situated on one of the base unit and the modular lighting unit;
      (2) at least partially transparent;
      (3) aligned with the light transmitter at least when the communications end of the modular lighting unit is received within the socket of the base unit,
   wherein the pedestal transmits light provided by the specimen to the light transmitter.

2. The photometer of claim 1 wherein the modular lighting unit further includes an optical adapter adjacent the light emitter, the optical adapter filtering and/or polarizing any light emitted from the light emitter.

3. The photometer of claim 1 wherein the modular lighting unit further includes one or more optical adapters, each optical adapter being situated between:
   a. the light emitter and the pedestal, or
   b. the pedestal and the light transmitter when the communications end of the modular lighting unit is installed within the socket,
   wherein each optical adapter filters and/or polarizes light traveling through the optical adapter.

4. The photometer of claim 1 wherein:
   a. the base unit further includes an arm having a cap thereon;
   b. when the communications end of the modular lighting unit is received within the socket of the base unit:
      (1) the cap is adjustably respaceable with respect to the pedestal, whereby the dimensions of a fluid specimen situated on the pedestal may be varied by respacing the cap with respect to the pedestal; and
      (2) the emitter end is situated between the arm and the socket of the base unit.

5. The photometer of claim 4 wherein the arm is pivotally affixed to the base unit.

6. The photometer of claim 4 wherein:
   a. the arm bears a linkage affixing the arm to the base unit, and
   b. the base unit further includes an actuator spaced from the linkage, the actuator bearing against a surface of the arm adjustably respace the cap with respect to the pedestal.

7. The photometer of claim 4 wherein:
   a. the base unit further includes a cap spaced from the light transmitter, the cap being adjustably respaceable from the light transmitter; and
   b. when the communications end of the modular lighting unit is received within the socket of the base unit, the light emitter is aligned to emit light outwardly from the emitter end toward the space between the cap and the light transmitter.

8. The photometer of claim 1 wherein the pedestal is affixed to the modular lighting unit, wherein the pedestal is situated upon the base unit adjacent the light transmitter when the communications end is received within the socket of the base unit.

9. The photometer of claim 1 wherein the modular lighting unit includes an emitter communications connection in communication with the light emitter, the emitter communications connection allowing communication of power to the light emitter to activate light emission therefrom.

10. The photometer of claim 9 wherein the emitter communications connection is situated on the communications end.

11. The photometer of claim 9 wherein:
    a. the emitter end includes two or more light emitters, each light emitter being aligned to emit light outwardly from the emitter end toward the light transmitter when the communications end is received within the socket of the base unit;
    b. light emitter is illuminated when power is supplied to a respective set of one or more of the leads.

12. The photometer of claim 1 wherein:
    a. the emitter end includes two or more light emitters, each light emitter being aligned to emit light outwardly from the emitter end toward the light transmitter when the communications end is received within the socket of the base unit;
    b. the modular lighting unit further includes one or more optical adapters, each optical adapter:
       (1) being situated to receive any light emitted from one of the light emitters, and
       (2) filtering and/or polarizing the light emitted from the light emitter.

13. The photometer of claim 1 further including a filter, wherein the filter receives light from the light emitter via the light transmitter.

14. The photometer of claim 1 further including two or more filters, wherein the filters are respositionable such that a selected one of the filters can be aligned to receive light from the light transmitter.

15. The photometer of claim 1 further including two or more of the modular lighting unit, wherein each of the different modular lighting units is constructed to emit light having different qualities toward the light transmitter when the communications end is received within the socket of the base unit.

16. A photometer including:
    a. a base unit having a socket defined extending inwardly from an outer surface of the base unit;
    b. a pedestal whereupon a specimen being situated, the pedestal being situated on the base unit adjacent the socket;
    c. a modular lighting unit having:
       (1) an emitter end;

(2) a communications end adjacent the emitter end, the communications end being configured to be complementarily received within the socket of the base unit;

(3) a light emitter upon the emitter end, the light emitter being aligned to emit light outwardly from the emitter end toward the pedestal when the communications end is received within the socket of the base unit;

(4) an emitter communications connection in communication with the light emitter, the emitter communications connection receiving power from the base unit and communicating the power to the light emitter when the communications end is received within the socket of the base unit.

17. The photometer of claim 16 wherein the modular lighting unit further includes an optical adapter adjacent the light emitter, the optical adapter filtering and/or polarizing any light emitted from the light emitter.

18. The photometer of claim 16 wherein:
  a. the modular lighting unit includes two or more light emitters upon the emitter end, the light emitters being aligned to emit light outwardly from the emitter end toward the pedestal when the communications end is received within the socket of the base unit;
  b. the emitter communications connection bears two or more leads, wherein one or more of the light emitters are illuminated when power is supplied to a selected one or more of the leads.

19. The photometer of claim 16:
  a. further including a filter, and
  b. wherein the pedestal:
    (1) receives light from any specimen situated on the pedestal, and
    (2) provides the light to the filter.

20. The photometer of claim 16:
  a. further including two or more filters;
  b. wherein the pedestal:
    (1) receives light from any specimen situated on the pedestal, and
    (2) provides the light along a transmission path to one of the filters;
  c. wherein at least one of:
    (1) the filters, and
    (2) the transmission path,
  may be adjusted with respect to each other such that the filters may be interchangeably situated along the transmission path.

21. The photometer of claim 16 wherein:
  a. the base unit includes:
    (1) a light transmitter therein, the light transmitter receiving light from the pedestal and any specimen thereon;
    (2) a detector receiving the light from the light transmitter;
  b. the pedestal is affixed to the modular lighting unit, wherein the pedestal is situated upon the base unit adjacent the light transmitter when the communications end is received within the socket of the base unit.

22. A photometer including:
  a. a modular lighting unit having:
    (1) an emitter end;
    (2) a communications end extending from the emitter end;
    (3) a light emitter situated on the emitter end, the light emitter being aligned to emit light outwardly from the emitter end;
    (4) an emitter communications connection in communication with the light emitter, the emitter communications connection allowing communication of power to the light emitter to activate light emission therefrom;
  b. a base unit having:
    (1) a base unit outer surface into which a socket extends, the socket being configured to complementarily receive the communications end of the modular lighting unit with the emitter end situated outside the socket adjacent the base unit outer surface;
    (2) a light transmitter within the base unit, the light transmitter receiving light from any specimen:
      (a) receiving light from the light emitter, and
      (b) situated adjacent the light emitter; and
    (3) a detector receiving the light from the light transmitter.

23. The photometer of claim 22 further including a pedestal whereupon a specimen being situated, the pedestal being:
  a. situated on one of the base unit and the modular lighting unit such that the pedestal is located adjacent the light transmitter when the communications end of the modular lighting unit is installed within the socket,
  b. at least partially transparent to light, whereby light received by the light transmitter from any specimen situated on the pedestal is received through the pedestal.

24. The photometer of claim 23 wherein the modular lighting unit further includes an optical adapter situated between the light emitter and the pedestal, wherein the optical adapter filters and/or polarizes any light emitted from the light emitter.

25. The photometer of claim 23 wherein the modular lighting unit further includes an optical adapter situated between the pedestal and the light transmitter when the communications end of the modular lighting unit is installed within the socket, wherein the optical adapter filters and/or polarizes any light transmitted from the pedestal to the light transmitter.

* * * * *